US012708291B2

(12) United States Patent
Tang

(10) Patent No.: US 12,708,291 B2
(45) Date of Patent: Aug. 18, 2026

(54) BREATHING AMPLITUDE DETECTION SYSTEM, METHOD, AND COMPUTER PROGRAM BASED ON MICRO FORCE DETECTION

(71) Applicant: Junyang Tang, Brooklyn, NY (US)

(72) Inventor: Junyang Tang, Brooklyn, NY (US)

( * ) Notice: Subject to any disclaimer, the term of this patent is extended or adjusted under 35 U.S.C. 154(b) by 316 days.

(21) Appl. No.: 18/520,574

(22) Filed: Nov. 28, 2023

(65) Prior Publication Data

US 2025/0169718 A1 May 29, 2025

(51) Int. Cl.
*A61B 5/113* (2006.01)
*A61B 5/00* (2006.01)

(52) U.S. Cl.
CPC .......... *A61B 5/1135* (2013.01); *A61B 5/6823* (2013.01); *A61B 5/7264* (2013.01); *A61B 5/7405* (2013.01); *A61B 5/742* (2013.01); *A61B 5/746* (2013.01); *A61B 2562/166* (2013.01)

(58) Field of Classification Search
CPC ... A61B 5/1135; A61B 5/6823; A61B 5/7264; A61B 5/7405; A61B 5/742; A61B 5/746; A61B 2562/166; A61B 5/113; A61B 5/081
See application file for complete search history.

(56) References Cited

U.S. PATENT DOCUMENTS

2004/0039294 A1* 2/2004 Sullivan .................. A61B 7/04 600/528
2011/0172551 A1* 7/2011 Al-Ali .................... A61B 7/003 600/529
2017/0018593 A1* 1/2017 Qiao ....................... H03M 3/30
2020/0234763 A1* 7/2020 Ge ...................... H03F 3/45475
2020/0300602 A1* 9/2020 Mochizuki ............ G01D 5/145

OTHER PUBLICATIONS

Electrical Engineering (Nov. 12, 2010) "https://electronics.stackexchange.com/questions/6621/flexiforce-pressure-sensor-with-positive-voltage" (Year: 2010).*
Tekscan (Flexiforce Sensors User Manual). Dec. 29, 2010 (Year: 2010).*

* cited by examiner

*Primary Examiner* — Christian Jang
(74) *Attorney, Agent, or Firm* — Yue (Robert) Xu; Apex Attorneys at Law, LLP

(57) ABSTRACT

This application provides a breathing amplitude detection solution based on micro force detection. In this solution, the breathing amplitude detection system includes a sensor, a processor, a sensor power supply circuit, an operational amplifier, and a feedback resistor. The sensor is a micro force detection sensor. The sensor can be connected to a user and sense the amplitude of the user's breathing movements. The sensor supply circuit is connected to the first terminal of the sensor and provides a reference voltage to the sensor. The second terminal of the sensor and the first terminal of the feedback resistor are connected to the first input terminal of the operational amplifier. The second terminal of the feedback resistor is connected to the output of the operational amplifier. The output of the operational amplifier is connected to the processor to transmit the measured voltage. The processor maps the measured voltages to discrete voltage values. The processor calculates the amplitude of the user's breathing movement based on the discrete voltage values. When the amplitude of the breathing movement falls below a preset threshold, the processor controls to issue an alarm signal.

11 Claims, 2 Drawing Sheets

BREATHING AMPLITUDE DETECTION SYSTEM, METHOD, AND COMPUTER PROGRAM BASED ON MICRO FORCE DETECTION

FIELD

The present disclosure relates to breathing amplitude detection, and more specifically to a breathing amplitude detection system, method, and computer program based on micro force detection.

BACKGROUND OF THE INVENTION

At present, a person's health status can be judged through changes in a person's breathing amplitude. By placing a gas detection or fluid detection device at a person's mouth, the person's breathing conditions can be detected. However, gas or fluid detection devices can affect the smoothness of human breathing.

SUMMARY OF THE INVENTION

Embodiments of the present disclosure provide a breathing amplitude detection system, method, and computer program based on micro force detection.

In a first aspect of the present disclosure, the present disclosure provides a breathing amplitude detection system based on small force detection, which is characterized in that the breathing amplitude detection system includes a sensor, a processor, a sensor power supply circuit, an operational amplifier, and a feedback resistor; the sensor is a micro force detection sensor, which can be connected to the user and senses the amplitude of the user's breathing movement; the sensor power supply circuit is connected to the first terminal of the sensor and provides a reference for the sensor voltage; the second terminal of the sensor and the first terminal of the feedback resistor are connected to the first input terminal of the operational amplifier; the second terminal of the feedback resistor is connected to the output terminal of the operational amplifier; the output of the operational amplifier is connected to the processor to transmit a measured voltage; the processor maps the first voltage value to discrete voltage values; the processor calculates the amplitude of the user's breathing movement based on the discrete voltage values; when the amplitude of the breathing movement is lower than a preset threshold, the processor controls to issue an alarm signal.

In a second aspect of the present disclosure, a breathing amplitude detection method based on micro force detection is provided. The method includes: obtaining a value of a reference voltage, the reference voltage being provided to a sensor by a sensor power supply circuit, and the sensor is a micro force detection sensor, the sensor can be connected to the user and sense the amplitude of the user's breathing movement; obtaining the value of the feedback resistor, the feedback resistor is connected to the operational amplifier; obtaining the measured voltage value of the output end of the operational amplifier; mapping the measured voltage to discrete voltage values; calculating the amplitude of the user's breathing movement according to the discrete voltage value; controlling to issue an alarm signal when the amplitude of the breathing movement is lower than a preset threshold.

In a third aspect of the present disclosure, there is provided a computer program product tangibly stored on a non-transitory computer-readable medium and including machine-executable instructions that, when executed, the machine is caused to perform the method of the second aspect of the present disclosure.

This Summary is provided to introduce a selection of concepts in a simplified form that are further described below in the Detailed Description. This Summary is not intended to identify key features or key features of the disclosure, nor is it intended to limit the scope of the disclosure.

BRIEF DESCRIPTION OF DRAWINGS

The above and other objects, features and advantages of the present disclosure will become more apparent by describing the exemplary embodiments of the present disclosure in more detail with reference to the accompanying drawings, wherein, in the exemplary embodiments of the present disclosure, the same reference numerals generally represent Same parts.

DETAILED DESCRIPTION OF THE INVENTION

Figure 1:
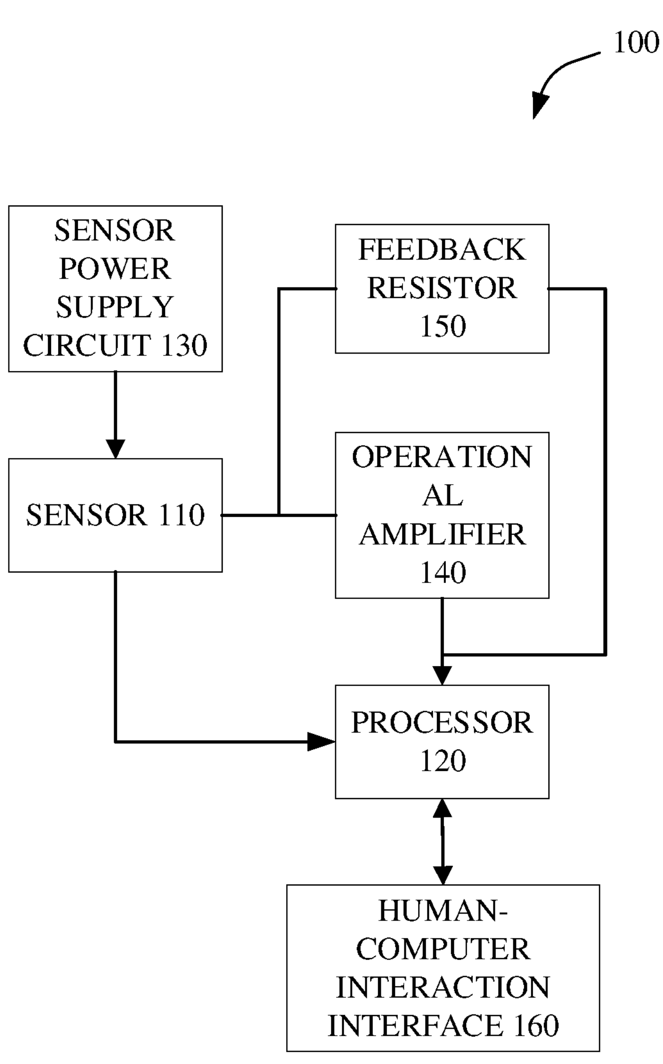
FIG. 1 shows a block diagram of a breathing amplitude detection system according to an embodiment of the present disclosure.

Preferred embodiments of the present disclosure will be described in more detail below with reference to the accompanying drawings. Although the preferred embodiments of the present disclosure are shown in the drawings, it should be understood that the present disclosure may be implemented in various forms and should not be limited to the embodiments set forth herein. Rather, these embodiments are provided so that this disclosure will be thorough and complete, and will fully convey the scope of the disclosure to those skilled in the art.

As used herein, the term "include" and its variations mean an open inclusion, ie, "including but not limited to." Unless otherwise stated, the term "or" means "and/or". The term "based on" means "based at least in part on." The terms "one example embodiment" and "an embodiment" mean "at least one example embodiment." The term "another embodiment" means "at least one additional embodiment". The terms "first," "second," etc. may refer to different or the same object. Other explicit and implicit definitions may be included below.

Currently, human breathing amplitude detection has some important application scenarios. For example, there are cases where a baby suddenly and unexpectedly stops breathing and dies during sleep, called sudden infant death syndrome (SIDS). There are also some elderly people who suddenly stop breathing in their sleep and need to monitor their breathing conditions during night sleep. In addition, people suffering from breathing infectious diseases also need to monitor their breathing conditions. By detecting changes in a person's breathing amplitude, it can help determine a person's health status. Currently, a person's breathing status can be detected by placing a gas detection or fluid detection device in a person's mouth. However, gas or fluid detection devices can affect the smoothness of human breathing.

In order to at least partially solve the above problems and other potential problems, example embodiments of the present disclosure provide a breathing amplitude detection system based on small force detection. The solution of the present disclosure may have less impact on users. The solution of the present disclosure can make breathing amplitude detection more convenient.

FIG. 1 shows a block diagram of a breathing amplitude detection system 100 according to an embodiment of the present disclosure. It should be understood that the structure and functionality of the breathing amplitude detection system 100 are described for illustrative purposes only and are not intended to imply any limitation on the scope of the present disclosure. That is, some components in the breathing amplitude detection system 100 may be omitted or replaced, and other components not shown may be added to the storage system 100. Embodiments of the present disclosure may be embodied in different structures and/or functions.

As shown in FIG. 1, the breathing amplitude detection system 100 includes a sensor 110, a processor 120, a sensor power supply circuit 130, an operational amplifier 140, and a feedback resistor 150.

The sensor 1 10 may be connected to the user and sense the amplitude of the user's breathing movements. The sensor power supply circuit 130 is connected to the first terminal of the sensor 110 and provides the sensor 110 with a reference voltage Vref. The second terminal of the sensor 1 10 and the first terminal of the feedback resistor 1 50 are connected to the first input terminal of the operational amplifier 140. The second terminal of the feedback resistor 1 50 is connected to the output terminal of the operational amplifier 140. The resistance of the feedback resistor is Rf, and the resistance of sensor 1 10 is Rs. The output of the operational amplifier 140 is connected to the processor 120 to transmit the measured voltage Vout.

Wherein, $Vout=-Vref*(Rf/Rs)$

Processor 120 maps measured voltage Vout to discrete voltage values Vwave. The processor 120 calculates the amplitude of the user's breathing movement based on the discrete voltage values. In some embodiments, the absolute value of the derivative of the discrete voltage value Vwave calculated with respect to time may be used as the value of the breathing movement amplitude.

Wherein, when the amplitude of the breathing movement is lower than a preset threshold, the processor 120 controls to issue an alarm signal. The preset threshold here can be set according to the breathing amplitude conditions of different human bodies.

In some non-limiting embodiments, processor 120 is an ATmega 328P microcontroller chip. It should be understood that other types of processors may also perform the functions of the processors 1 to 20 of the present disclosure. Sensors 1 10 are available with FlexiForce A201 micro force sensor. It should be understood that other sensors that can implement force detection can also implement the functions of the sensors 1 to 10 of the present disclosure.

In some embodiments, the reference voltage provided by the sensor power supply circuit 130 is a negative voltage value. In a non-limiting embodiment, the sensor power supply circuit 130 may include a LM317 three-terminal adjustable voltage regulator chip, a DC power supply, a capacitor, a resistor and other specific devices. The output value of the voltage can be adjusted between −0.5 V and −1.25 V.

In some embodiments, the inverse closed-loop operational amplifier circuit includes components such as an operational amplifier 140, a feedback resistor 150, and a capacitor. The resistance value of the feedback resistor can be set from 10 K ohms to 100 K ohms. Through the reverse closed-loop operational amplifier circuit, the signal output by the sensor 110 can be amplified to facilitate processing by the processor 120. In some non-limiting embodiments, the output of operational amplifier 140 is connected to an analog-to-digital conversion pin of processor 120. In addition, the VCC port of the processor 120 is used to provide the operating voltage for the operational amplifier 140.

In some embodiments, the first voltage value is proportional to the amplitude of the user's breathing movement. That is, through changes in the first voltage value, changes in the human body's breathing amplitude can be detected.

In some embodiments, controlling the processor 120 to issue an alarm signal includes at least one of the following operations: controlling the processor to issue an audible alarm, controlling an optical alarm, or transmitting an alarm signal to a remote device through a communication device. For example, light-emitting diodes can be used to generate optical alarms. In addition, the detection information can be transmitted to other remote devices by setting up a wireless communication module.

In some embodiments, the range of the first voltage value is set to 0 to 5V. In some embodiments, the range of discrete voltage values is set to 0 to 1023.

In some embodiments, the sensor 1 10 is in the form of a flexible printed circuit that is attached to the user's chest or abdomen. The flexible printed circuit can be mounted on a belt and then worn on the body.

In some embodiments, the breath detection system also includes a human-computer interaction interface 160. For example, the user can check his/her breathing status through the human-computer interaction interface 160, or set a time period for monitoring breathing. In a non-limiting embodiment, the frequency of transmitting breathing conditions to external devices can also be set through the human-computer interaction interface 160.

Figure 2:
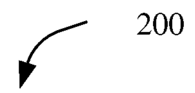
FIG. 2 shows a flowchart of a breathing amplitude detection method according to an embodiment of the present disclosure.
Figure 2:
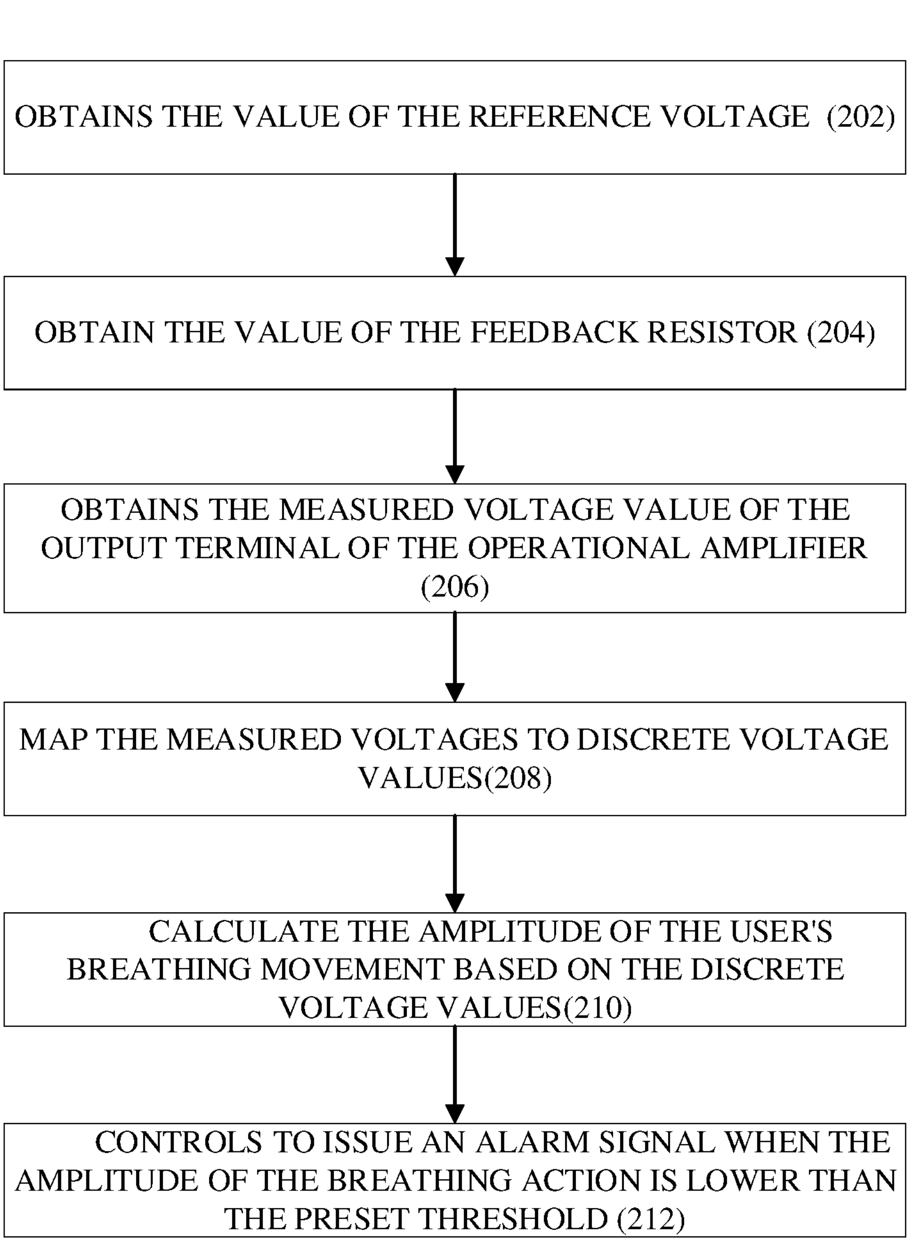

FIG. 2 shows a flowchart of a method 200 for breathing amplitude detection according to an embodiment of the present disclosure. It should be understood that method 200 may also include additional steps not shown and/or illustrated actions may be omitted, and the scope of the present disclosure is not limited in this respect.

At 202, the processor 120 obtains the value of the reference voltage. The reference voltage is provided to the sensor 110 by the sensor power supply circuit 130. The sensor 110 is a small force detection sensor. The sensor 110 can be connected to the user and sense the user. The range of breathing movements.

At 204, the processor 120 obtains the value of the feedback resistor 150, which is connected to the operational amplifier 140.

At 206, the processor 120 obtains the measured voltage value of the output terminal of the operational amplifier 140. After the amplification effect of the operational amplifier 140, the signal with a smaller amplitude is amplified into a signal with a larger amplitude.

At 208, processor 120 maps the measured voltages to discrete voltage values. By discretizing analog signals, subsequent processing can be converted into digital signal processing.

At 210, the processor 120 calculates the amplitude of the user's breathing movement based on the discrete voltage values. For example, by calculating the derivative of the discrete voltage value with respect to time, it can be used as the amplitude of the user's breathing movement.

At 212, the processor 120 controls to issue an alarm signal when the amplitude of the breathing action is lower than the preset threshold.

Through the solution of the present disclosure, breathing amplitude detection can be more convenient.

The disclosure may be a method, system and/or computer program product. A computer program product may include a computer-readable storage medium having thereon computer-readable program instructions for performing various aspects of the present disclosure.

Computer-readable storage media may be tangible devices that can retain and store instructions for use by an instruction execution device. The computer-readable storage medium may be, for example, but not limited to, an electrical storage device, a magnetic storage device, an optical storage device, an electromagnetic storage device, a semiconductor storage device, or any suitable combination of the above. More specific examples (non-exhaustive list) of computer-readable storage media include: portable computer disks, hard disks, random access memory (RAM), read-only memory (ROM), erasable programmable read-only memory (EPROM) or flash memory), flash media SSD, PCM SSD, 3D cross memory (3DXPoint), static random access memory (SRAM), portable compact disk read-only memory (CD-ROM), digital versatile disk (DVD), memory stick, A floppy disk, a mechanical encoding device, such as a punched card or a raised-in-groove structure with instructions stored thereon, and any suitable combination of the above. As used herein, computer-readable storage media are not to be construed as transient signals per se, such as radio waves or other freely propagating electromagnetic waves, electromagnetic waves propagating through waveguides or other transmission media (e.g., light pulses through fiber optic cables), or through electrical wires. transmitted electrical signals.

Computer-readable program instructions described herein may be downloaded from a computer-readable storage medium to various computing/processing devices, or to an external computer or external storage device over a network, such as the Internet, a local area network, a wide area network, and/or a wireless network. The network may include copper transmission cables, fiber optic transmission, wireless transmission, routers, firewalls, switches, gateway computers, and/or edge servers. A network adapter card or network interface in each computing/processing device receives computer-readable program instructions from the network and forwards the computer-readable program instructions for storage on a computer-readable storage medium in the respective computing/processing device.

Computer program instructions for performing operations of the present disclosure may be assembly instructions, instruction set architecture (ISA) instructions, machine instructions, machine-related instructions, microcode, firmware instructions, state setting data, or instructions in one or more programming languages. Source code or object code written in any combination of programming languages including object-oriented programming languages-such as Smalltalk, C++, etc., and conventional procedural programming languages-such as the "C" language or similar programming languages. The computer-readable program instructions may execute entirely on the user's computer, partly on the user's computer, as a stand-alone software package, partly on the user's computer and partly on a remote computer or entirely on the remote computer or server implement. In situations involving remote computers, the remote computer can be connected to the user's computer through any kind of network, including a local area network (LAN) or a wide area network (WAN), or it can be connected to an external computer (such as an Internet service provider through the Internet). connect). In some embodiments, by utilizing state information of computer-readable program instructions to personalize an electronic circuit, such as a programmable logic circuit, a field programmable gate array (FPGA), or a programmable logic array (PLA), the electronic circuit can Computer readable program instructions are executed to implement various aspects of the disclosure.

The invention claimed is:

1. A breathing amplitude detection system based on micro force detection, characterized in that the breathing amplitude detection system includes a sensor, a processor, a sensor power supply circuit, an operational amplifier, and a feedback resistor, characterized in that:

the sensor is a small force detection sensor, which is connectable to a user and sense the amplitude of the user's breathing movement;

the sensor power supply circuit is connected to the first terminal of the sensor and provides a reference voltage to the sensor;

the second terminal of the sensor and the first terminal of the feedback resistor are connected to the first input terminal of the operational amplifier;

the second terminal of the feedback resistor is connected to the output terminal of the operational amplifier;

the output of the operational amplifier is connected to the processor for transmitting a measured voltage;

the processor maps the measured voltages to discrete voltage values;

the processor calculates the amplitude of the user's breathing movement based on an absolute value of a derivative of the discrete voltage values with respect to time;

when the amplitude of the breathing movement is lower than a preset threshold, the processor controls to issue an alarm signal.

2. The breathing amplitude detection system according to claim 1, wherein the reference voltage provided by the sensor power supply circuit is a negative voltage value.

3. The breathing amplitude detection system according to claim 1, wherein the operational amplifier, the feedback resistor, and other components are configured as an inverse closed-loop operational amplifier circuit.

4. The breathing amplitude detection system according to claim 1, characterized in that, the first voltage value is proportional to the amplitude of the user's breathing movement.

5. The breathing amplitude detection system according to claim 1, wherein the processor controlling to issue an alarm signal includes at least one of the following operations: controlling the processor to issue an audible alarm, controlling to issue an optical alarm, or controlling the alarm signal through a communication device transmits the alarm signal to a remote device.

6. The breathing amplitude detection system according to claim 1, wherein the range of the discrete voltage value is set to 0 to 1023.

7. The breathing amplitude detection system according to claim 1, wherein the range of the first voltage value is set to 0V to 5 V.

8. The breathing amplitude detection system according to claim 1, wherein the sensor is in the form of a flexible printed circuit, and the flexible printed circuit is attached to the chest or abdomen of the user.

9. The breathing amplitude detection system according to claim 1, characterized in that the breath detection system further includes a human-computer interaction interface.

10. A breathing amplitude detection method based on small force detection, characterized in that the method includes:

obtaining the value of the reference voltage, the reference voltage is provided to the sensor by the sensor power supply circuit, the sensor is a small force detection sensor, the sensor can be connected to the user and senses the amplitude of the user's breathing movement;

obtaining the value of the feedback resistor, which is connected to the operational amplifier;

obtaining the measured voltage value of the output terminal of the operational amplifier;

mapping the measured voltages to discrete voltage values;

calculating the amplitude of the user's breathing movement based on an absolute value of a derivative of the discrete voltage values with respect to time;

when the amplitude of the breathing action is lower than the preset threshold, controlling to issue an alarm signal.

11. A computer program product tangibly stored on a non-transitory computer-readable medium and comprising machine-executable instructions that, when executed, cause the machine to perform the method according to claim 10.

* * * * *